US012586688B2

(12) United States Patent
Sakurada et al.

(10) Patent No.: US 12,586,688 B2
(45) Date of Patent: Mar. 24, 2026

(54) INFORMATION PROCESSING SYSTEM, INFORMATION PROCESSING METHOD, AND RECORDING MEDIA

(71) Applicant: TOYOTA JIDOSHA KABUSHIKI KAISHA, Toyota (JP)

(72) Inventors: Shin Sakurada, Toyota (JP); Kazuya Nishimura, Anjo (JP); Takumi Fukunaga, Nagoya (JP); Josuke Yamane, Nisshin (JP); Soutaro Kaneko, Nagoya (JP); Rio Minagawa, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 1324 days.

(21) Appl. No.: 17/343,336

(22) Filed: Jun. 9, 2021

(65) Prior Publication Data

US 2021/0407691 A1 Dec. 30, 2021

(30) Foreign Application Priority Data

Jun. 26, 2020 (JP) ................................. 2020-110367

(51) Int. Cl.
*G16H 50/80* (2018.01)
*G01C 21/36* (2006.01)
(Continued)

(52) U.S. Cl.
CPC ......... *G16H 50/80* (2018.01); *G01C 21/3617* (2013.01); *G16H 10/60* (2018.01); *G16H 50/20* (2018.01); *G16H 50/30* (2018.01)

(58) Field of Classification Search
CPC ........ G16H 50/80; G16H 10/60; G16H 50/20; G16H 50/30; G16H 15/00; G01C 21/3617; H04W 4/029; H04L 67/12
See application file for complete search history.

(56) References Cited

U.S. PATENT DOCUMENTS

| | | | |
|---|---|---|---|
| 6,738,808 B1 * | 5/2004 | Zellner | H04M 1/72445 709/219 |
| 10,303,843 B2 * | 5/2019 | Bitran | G16H 50/80 |

(Continued)

FOREIGN PATENT DOCUMENTS

| | | |
|---|---|---|
| CN | 107924716 A | 4/2018 |
| CN | 109727681 A | 5/2019 |

(Continued)

*Primary Examiner* — Karlheinz R. Skowronek
*Assistant Examiner* — Nidhi Dharithressan
(74) *Attorney, Agent, or Firm* — Oliff PLC

(57) ABSTRACT

An information processing system includes a first information processing apparatus, and a plurality of second information processing apparatuses. The first information processing apparatus acquires movement history information on an infected person with a predetermined infectious disease, identifies, based on the movement history information, a first place that the infected person visited and a first visit date and time, and notifies the second information processing apparatus associated with the first place of information about the first place and the first visit date and time. Each second information processing apparatus identifies, based on visit history information including a visit date and time of the predetermined place by users who are associated with the predetermined place, a first user who visited the first place on the first visit date and time, and notify the first user of possibility of being infected with the predetermined infectious disease.

13 Claims, 8 Drawing Sheets

(51) Int. Cl.
    *G16H 10/60*     (2018.01)
    *G16H 50/20*     (2018.01)
    *G16H 50/30*     (2018.01)

(56)                   References Cited

U.S. PATENT DOCUMENTS

| 2017/0039339 | A1 | 2/2017 | Bitran et al. |
| 2021/0043330 | A1 | 2/2021 | Ikeshima |
| 2023/0121997 | A1 | 4/2023 | Dang et al. |

FOREIGN PATENT DOCUMENTS

| CN | 111027525 A | * | 4/2020 | .......... G06V 10/764 |
| JP | 2020-027610 A | | 2/2020 | |

* cited by examiner

*FIG. 4*

SHOP-VISIT HISTORY INFORMATION DATABASE

| TIMESTAMP | SHOP ID | CUSTOMER ID | TYPE OF EVENT |
|---|---|---|---|
|  |  |  | CHECK-IN |
|  |  |  | BUY |
|  |  |  |  |

.
.
.

INFORMATION PROCESSING SYSTEM, INFORMATION PROCESSING METHOD, AND RECORDING MEDIA

CROSS REFERENCE TO RELATED APPLICATION

This application claims the benefit of Japanese Patent Application No. 2020-110367, filed on Jun. 26, 2020, which is hereby incorporated by reference herein in its entirety.

BACKGROUND

Technical Field

The present disclosure relates to an information processing system, an information processing method, and a recording medium.

Description of the Related Art

There is disclosed a technology for acquiring the level of an infection risk of an infectious disease in a region based on an infection alert level that is obtained from an audio signal analyzed by an audio recognition apparatus, and identifying the infection risk on a per-region basis and in a timely manner (for example, Patent document 1).

CITATION LIST

[Patent document 1] Japanese Patent Laid-Open No. 2020-027610

An object of the present disclosure is to provide an information processing system, an information processing method, and a program that are capable of notifying an individual of the possibility of being infected with a predetermined infectious disease.

SUMMARY

An aspect of the present disclosure is an information processing system comprising a first information processing apparatus, and a plurality of second information processing apparatuses that are associated with respective predetermined places, wherein the first information processing apparatus includes a first controller configured to:
acquire movement history information on an infected person who is proven to be infected with a predetermined infectious disease,
identify, based on the movement history information, a first place that the infected person visited and a first visit date and time by the infected person, and
notify a second information processing apparatus associated with the first place of information about the first place and information about the first visit date and time, and
the plurality of second information processing apparatuses each include a second controller configured to:
identify, based on visit history information including a visit date and time of a predetermined place by a user who is associated with the predetermined place, a first user who visited the predetermined place as the first place on the first visit date and time, and
notify the first user of possibility of being infected with the predetermined infectious disease.

Another aspect of the present disclosure is an information processing method that is performed by a first information processing apparatus, and a plurality of second information processing apparatuses that are associated with respective predetermined places, wherein the first information processing apparatus is configured to:
acquire movement history information on an infected person who is proven to be infected with a predetermined infectious disease,
identify, based on the movement history information, a first place that the infected person visited and a first visit date and time, and
notify a second information processing apparatus associated with the first place of information about the first place and information about the first visit date and time, and
the plurality of second information processing apparatuses are each configured to:
identify, based on visit history information including a visit date and time of the predetermined place by a user who is associated with the predetermined place, a first user who visited the predetermined place as the first place on the first visit date/time, and
notify the first user of possibility of being infected with the predetermined infectious disease.

Another aspect of the present disclosure is a non-transitory computer-readable recording medium stored with a program for causing a computer to:
receive, from a second information processing apparatus that is associated with a first place that an infected person who is proven to be infected with a predetermined infectious disease visited, a notification about possibility of a user of the computer being infected with the predetermined infectious disease due to being at the first place on a first visit date and time when the infected person visited the first place, wherein the first place and the first visit date and time are identified based on movement history information on the infected person, and
output the notification.

According to the present disclosure, an individual may be notified of the possibility of being infected with a predetermined infectious disease.

BRIEF DESCRIPTION OF THE DRAWINGS

FIG. 4 is a diagram illustrating an example of information that is held in the shop-visit history information database;

DESCRIPTION OF THE EMBODIMENTS

Figure 1:
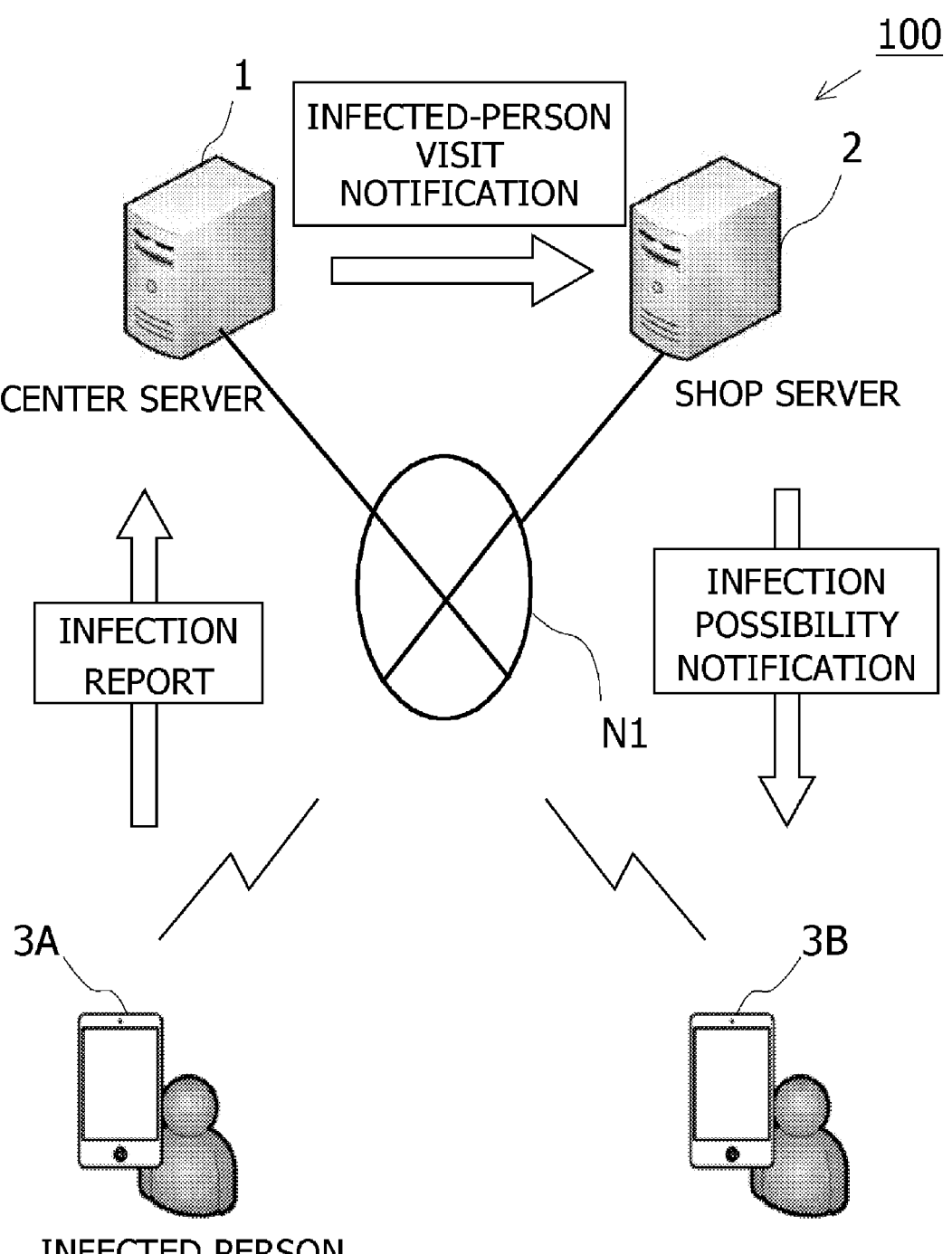
FIG. 1 is a diagram illustrating an example of a system configuration of an infection possibility notification system according to a first embodiment.

An aspect of the present disclosure is an information processing system including a first information processing apparatus and a plurality of second information processing apparatuses. The second information processing apparatuses are each associated with a predetermined place. The first information processing apparatus includes a first controller configured to acquire movement history information on an infected person who is proven to be infected with a predetermined infectious disease, identify, based on the movement history information, a first place that the infected person visited and a first visit date and time, and notify the second information processing apparatus associated with the first place that is identified of information about the first place and information about the first visit date and time. The plurality of second information processing apparatuses each include a second controller configured to identify, based on visit history information including a visit date/time of the predetermined place by a user who is associated with the predetermined place, a first user who visited the predetermined place as the first place on the first visit date and time, and notify the first user of possibility of being infected with the predetermined infectious disease.

The first information processing apparatus and the second information processing apparatus are each a server, for example. The first information processing apparatus may be an apparatus that operates as the second information processing apparatus. The first controller and the second controller are each a processor such as a central processing unit (CPU), for example. A predetermined place that the second information processing apparatus is associated with is a shop, a facility, a vehicle for public transportation, or the like, for example. That is, the second information processing apparatus is an apparatus that is included in systems for managing those listed above.

Another aspect of the present disclosure is a non-transitory computer-readable medium stored with a program to be executed by a computer. This program causes a computer to receive, from a second information processing apparatus that is associated with a first place that an infected person who is proven to be infected with a predetermined infectious disease visited, a notification about possibility of a user of the computer being infected with the predetermined infectious disease due to being at the first place on a first visit date and time when the infected person visited the first place, wherein the first place and the first visit date and time are identified based on the movement history information on the infected person, and output the notification. The computer that executes the program is a user terminal, for example.

According to each aspect of the present disclosure described above, a first user who was possibly at the same place and at the same time as an infected person may be identified based on the movement history information on the infected person, and the first user may be individually notified of the possibility of being infected with the infectious disease. Furthermore, personal information on the first user is not made known to apparatuses other than the corresponding second information processing apparatus, and thus, people other than the first user may be prevented from knowing that the first user is possibly infected with the predetermined infectious disease.

Furthermore, in an aspect of the present disclosure, the movement history information on an infected person may be anonymous information. That is, personal information on an infected person is not included in the movement history information. Accordingly, that the user corresponding to the movement history information is an infected person is not made known to other users, and privacy may be protected.

Furthermore, according to an aspect of the present disclosure, the movement history information may include location information and an acquisition date and time of the location information. In this case, the first controller of the first information processing apparatus may identify the first place and the first visit date and time based on the movement history information on the infected person and map information. The location information is, but not limited to, latitude and longitude that are acquired by a location sensor installed in a user terminal carried by the infected person, for example. When the movement history information is the location information, more detailed information, such as a duration of a stay of the infected person at the first place, may be acquired, for example.

Furthermore, according to an aspect of the present disclosure, at least one of the movement history information and the visit history information may be information about a payment history. Furthermore, at least one of the movement history information and the visit history information may be history information on a visit to the predetermined place recorded by a user terminal through an application related to the predetermined place. Furthermore, at least one of the movement history information and the visit history information may be boarding reservation information including at least a transportation number or a train name of public transportation and a boarding date. In this case, the information about the first place may be information indicating the transportation number or the train name. The information about the first visit date and time may be information indicated by the transportation number or the train name and the boarding date. Public transportation may be trains, buses, and airplanes, for example. By using various information pieces as described above as the movement history information, a place visited by the infected person may be more accurately or more efficiently identified. Moreover, the location information is sometimes not acquired by the location sensor due to invalid setting, radio interference or the like, and thus, when the movement history information is varied, the movement history information may be acquired without any loss.

Furthermore, according to an aspect of the present disclosure, the second controller of the second information processing apparatus may identify, as the first user, a user corresponding to the visit history information that includes a visit date and time of the predetermined place that is included in a predetermined period of time including the first visit date and time. For example, even though there is just one piece of the movement history information on the infected person regarding the first place, the infected person may stay at the first place for a long period of time. Accordingly, it is possible to reduce the loss of finding a first user who was possibly at the same place and at the same time as the infected person.

Furthermore, according to an aspect of the present disclosure, the first controller of the first information processing apparatus may further be configured to receive an infection report from a user terminal of the infected person, together with the movement history information, and assign identification information to the infection report. This enables management to be performed on a per-infection-report basis. Furthermore, because the identification information is not assigned to the infected person, the infected person may be prevented from being identified.

Furthermore, in the case where the identification information is assigned to the infection report, the first controller of the first information processing apparatus may be further configured to notify the user terminal of the infected person of the identification information on the infection report. Furthermore, the first controller of the first information processing apparatus may notify the second information processing apparatus associated with the first place of the identification information, together with the first visit date and time. The second controller of the second information processing apparatus may notify a user terminal of the first user of the identification information, together with the possibility of being infected with the predetermined infectious disease. In the case where the infected person himself/herself is included as the first user, notifying the user terminal of the first user of the identification information on the infection report allows the notification about the possibility of being infected to be recognized as the notification about the possibility of being infected that is based on the report from the infected person himself/herself.

Moreover, the program according to the aspect of the present disclosure may cause a computer to transmit the infection report to the first information processing apparatus, and receive, from the first information processing apparatus, first identification information assigned to the infection report. Furthermore, the program may cause the computer to receive the notification about possibility of being infected with the infectious disease from one of the plurality of second information processing apparatuses, and discard the notification in a case where the identification information received together with the notification matches the first identification information, and output the notification in a case where the identification information received together with the notification does not match the first identification information. For the infected person reporting infection, being notified of the possibility of being infected can be irritating. However, such irritation due to the infected person reporting infection being notified of the possibility of being infected may be reduced in the above manner.

In the following, an embodiment of the present disclosure will be described with reference to the drawings. The configuration of the embodiment described below is an example, and the present disclosure is not limited to the configuration of the embodiment.

First Embodiment

FIG. 1 is a diagram illustrating an example of a system configuration of an infection possibility notification system 100 according to a first embodiment. The infection possibility notification system 100 is a system that notifies of possibility of being infected to a user who was possibly at the same place and at the same time as an infected person with a predetermined infectious disease. For example, the infection possibility notification system 100 includes a center server 1, a shop server 2, a user terminal 3A, and a user terminal 3B. However, the infection possibility notification system 100 may include a plurality of user terminals without being limited to the user terminal 3A and the user terminal 3B. In the following, in the case of not distinguishing between the two, the user terminal 3A and the user terminal 3B will be simply referred to as "user terminal(s) 3". Furthermore, the infection possibility notification system 100 includes a plurality of shop servers 2, and a server or a system in a different jurisdiction from the center server 1 of a management system or the like of a company or an organization, but in the first embodiment, one shop server 2 is described to be included for the sake of simplicity.

The center server 1, the shop server 2, the user terminal 3A, and the user terminal 3B are connected to a network N1 and are capable of communicating through the network N1. The network N1 is the Internet, for example.

The center server 1 is a server that is managed by an administrator of the infection possibility notification system 100. The shop server 2 is a server that manages information about a shop A, for example. Information that is managed by the shop server 2 includes customer information on the shop A, information about purchase of goods, and the like, for example. The shop server 2 is a server that is managed by a company or an organization that is registered with the infection possibility notification system 100.

The user terminal 3A is assumed to be a user terminal of an infected person with a predetermined infectious disease. The user terminal 3B is assumed to be a user terminal of a user who is registered with the shop A as a customer. An application of the infection possibility notification system 100 is installed in each user terminal 3, for example.

When proven to be infected with the predetermined infectious disease, the infected person performs an infection report through the user terminal 3A. Information about the type of the infectious disease, a date of first symptoms, a date of diagnosis of infection and the like is also input at the time of an input operation for the infection report, for example. When an operation of the infection report is input by a user, the user terminal 3A collects movement history information on the infected person for a predetermined period of time, and transmits the same to the center server 1, together with the infection report. At this time, the infection report is performed anonymously, and information that enables identification of the infected person is not transmitted. Information that enables identification of the infected person includes a name, an address, a telephone number, an email address and the like, for example. The movement history information includes at least date and time (hereinafter referred "date/time") information and place information, for example. The movement history information is history information on an acquisition of location information, visit history information regarding a predetermined shop, reservation history information regarding public transportation, information on a payment with electronic money and the like that are held by the user terminal 3A, for example.

When the infection report and the movement history information are received from the user terminal 3A, the center server 1 identifies the place that the infected person visited and the visit date/time. The place that is identified is a place that can be used by an unspecified large number of people, such as a shop, a facility, public transportation and the like. One or a plurality of visited places may be identified. The center server 1 transmits, to a server that manages the place that is visited by the infected person, an infected-person visit notification notifying of visit of the infected person. Information about the visited place of the infected person and information about the visit date/time are also notified together with the infected-person visit notification. The visited place of the infected person is an example of "first place". The visit date/time by the infected person is an example of "first visit date/time".

When the infected-person visit notification is received from the center server 1, the shop server 2 identifies customers who visited the shop A on the visit date/time by the infected person. The shop server 2 transmits, to the user terminal 3B of a customer who is identified, an infection possibility notification notifying of the possibility of being infected with the predetermined infectious disease. The customer is an example of "user who is associated with the predetermined place".

When the infection possibility notification is received from the center server 1, the user terminal 3B outputs the infection possibility notification. A user of the user terminal 3B, that is, the customer who visited the shop A at the same time as the infected person, may thereby be notified of possible infection.

Figure 2:
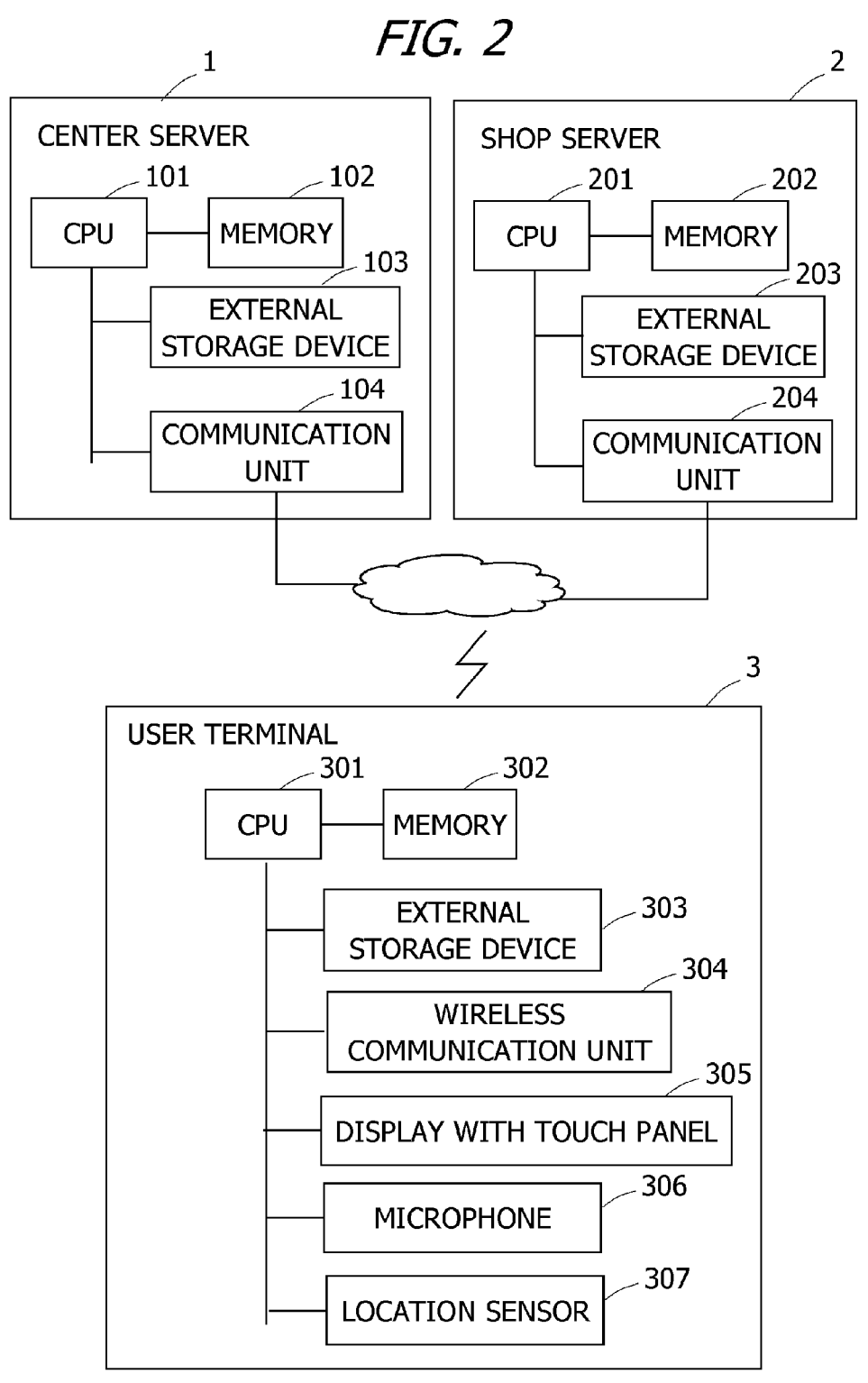
FIG. 2 is an example of hardware configurations of the center server, the shop server, and the user terminal.

FIG. 2 is an example of hardware configurations of the center server 1, the shop server 2, and the user terminal 3. As the hardware configuration, the center server 1 includes a CPU 101, a memory 102, an external storage device 103, and a communication unit 104. The memory 102 and the external storage device 103 are each a computer-readable storage medium. The center server 1 is an example of "first information processing apparatus".

The external storage device 103 stores various programs, and data to be used by the CPU 101 at the time of execution of each program. For example, the external storage device 103 is an erasable programmable ROM (EPROM) or a hard disk drive. Programs held in the external storage device 103 include an operating system (OS), a control program of the infection possibility notification system 100, and other various application programs, for example.

The memory 102 is a memory that provides the CPU 101 with a storage area where the program stored in the external storage device 103 is to be loaded and a work area, and that is used as a buffer. The memory 102 includes a semiconductor memory such as a read only memory (ROM) and a random access memory (RAM), for example.

The CPU 101 performs various processes by loading the OS and various application programs held in the external storage device 103 into the memory 102 and executing the same. The number of CPUs 101 may be one or more. The CPU 101 is an example of "first controller".

The communication unit 104 is a wired network card for a local area network (LAN) or a dedicated line, for example, and the communication unit 104 connects to the network N1 through an access network such as the LAN. The hardware configuration of the center server 1 is not limited to the one illustrated in FIG. 2.

As the hardware configuration, the shop server 2 includes a CPU 201, a memory 202, an external storage device 203, and a communication unit 204. The shop server 2 is an example of "second information processing apparatus". The CPU 201, the memory 202, the external storage device 203, and the communication unit 204 are the same as the CPU 101, the memory 102, the external storage device 103, and the communication unit 104. The external storage device 203 stores a program for coordinating with the center server 1 of the infection possibility notification system 100.

As the hardware configuration, the user terminal 3 includes a CPU 301, a memory 302, an external storage device 303, a wireless communication unit 304, a display 305 with a touch panel, a microphone 306, and a location sensor 307, for example. However, FIG. 2 extracts and displays hardware related to the infection possibility notification system 100, and the hardware configuration of the user terminal 3 is not limited to the one illustrated in FIG. 2.

The CPU 301, the memory 302, and the external storage device 303 are the same as the CPU 101, the memory 102, and the external storage device 103, respectively, and a description thereof is omitted. The external storage device 303 stores an application for a client of the infection possibility notification system 100. The CPU 301 is an example of "third controller".

The wireless communication unit 304 is a wireless communication circuit compatible with 5th generation (5G), long term evolution (LTE), LTE-Advanced or 3rd generation (3G) mobile communication or with a wireless communication method such as WiFi, for example. The wireless communication unit 304 connects to an access network through wireless communication, and connects to the network N1 through the access network.

The display 305 with a touch panel and the microphone 306 are examples of an input device. A user operation is input to the display 305 with a touch panel or the microphone 306. Furthermore, the display 305 with a touch panel is an example of an output device, and outputs a notification of possible infection, for example. The user terminal 3 may, in addition, include a speaker as an example of the output device.

The location sensor 307 is a sensor that acquires location information. For example, the location sensor 307 is a global positioning system (GPS) receiver. Location information that is acquired by the location sensor 307 is latitude and longitude, for example.

Additionally, the hardware configurations of the center server 1, the shop server 2, and the user terminal 3 are not limited to those illustrated in FIG. 2.

Figure 3:
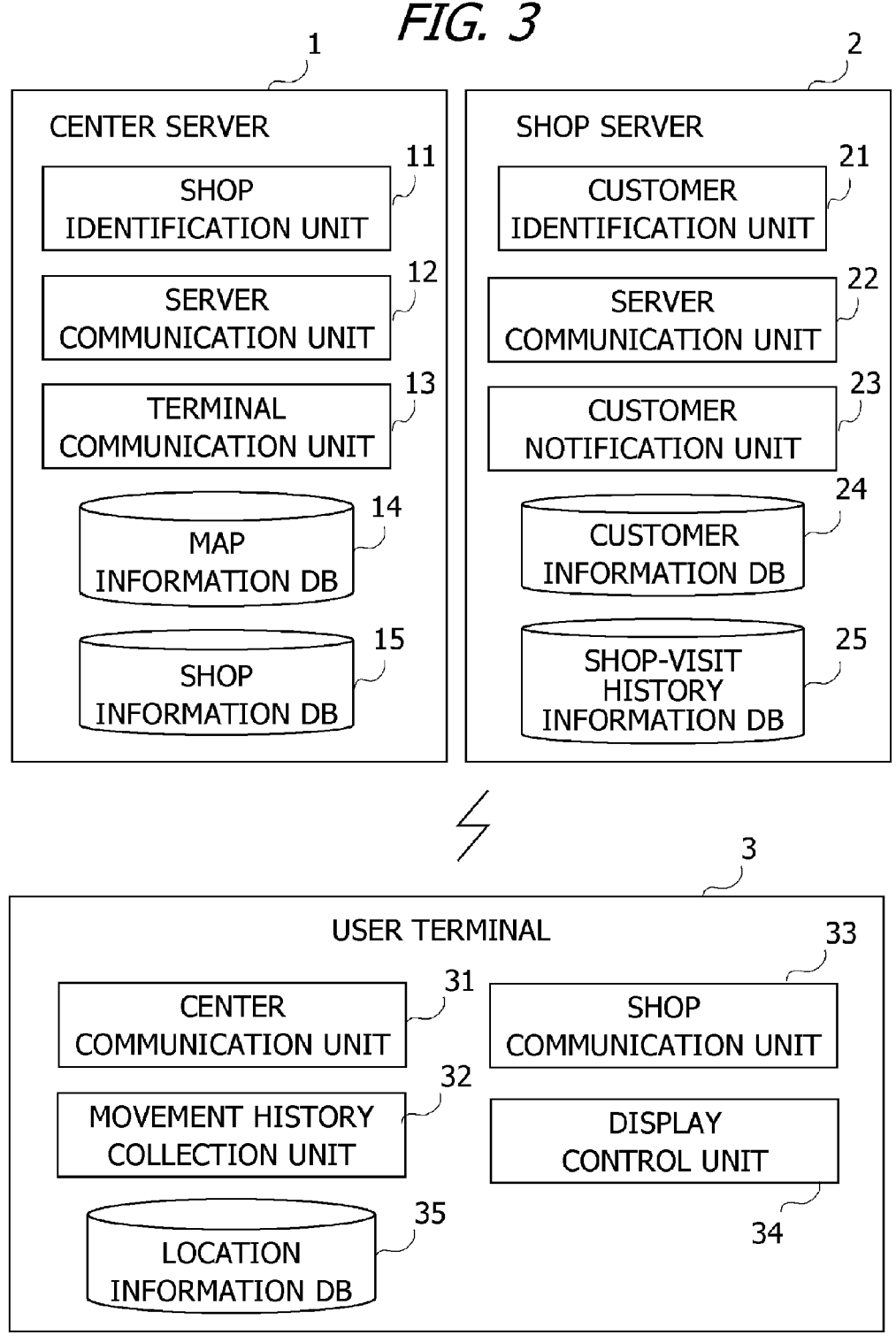
FIG. 3 is a diagram illustrating an example of functional configurations of the center server, the shop server, and the user terminal.

FIG. 3 is a diagram illustrating an example of functional configurations of the center server 1, the shop server 2, and the user terminal 3. As the functional configuration, the user terminal 3 includes a center communication unit 31, a movement history collection unit 32, a shop communication unit 33, a display control unit 34, and a location information DB 35. These functional elements are implemented by the CPU 301 of the user terminal 3 executing corresponding programs.

The center communication unit 31 communicates with the center server 1. For example, the center communication unit 31 receives an input from the movement history collection unit 32, and transmits an infection report and the movement history information to the center server 1.

The movement history collection unit 32 receives input of a user operation for an infection report, and collects the movement history information on the user of the user terminal 3 for a predetermined period of time. The type of the infectious disease and the date of diagnosis of infection or the date of first symptoms are input together with the infection report, for example. The collection period of the movement history information is a period from the start of an incubation period of the infectious disease to the date of first symptoms or the date of diagnosis of infection, for example. However, the collection period of the movement history information is not limited to the above, and a predetermined number of days from the date of first symptoms or the date of diagnosis of infection may also be added to the period described above.

The movement history information includes at least date/time information and place information. For example, the movement history information may be history information on an acquisition of location information, shop-visit history information regarding a predetermined shop, reservation history information regarding public transportation, payment history information regarding electronic money and the like that are held by the user terminal 3A.

The location information is acquired by the location sensor 307 every predetermined period of time, and is stored in the location information DB 305. The history information on an acquisition of the location information includes the location information as the place information, and the acquisition date/time of the location information as the date/time information, for example.

For example, the shop-visit history information regarding a predetermined shop may be history information on a check-in, history information on an addition or use of points, and the like obtained through an application associated with the shop. The shop-visit history information regarding a predetermined shop includes information indicating the shop as the place information, and the date/time of check-in or addition or use of points as the date/time information, for example.

The reservation history information regarding public transportation is information about boarding reservation for an express train, an express bus or an airplane made through an application of the corresponding public transportation, for example. The reservation history information regarding public transportation includes the transportation number or the train name as the place information, and the boarding date/time as the date/time information, for example. Information about the seat may also be included as the place information.

The payment history information regarding electronic money is history information on a payment made through an application for payment by a credit card, a debit card, an IC card, a QR code (registered trademark) or the like, for example. The information on a payment with electronic money includes information about a shop or the like receiving the payment as the place information, and a payment date/time as the date/time information, for example.

The movement history collection unit 32 acquires the various pieces of movement history information described above through various applications installed in the user terminal 3, for example. The movement history collection unit 32 outputs the infection report and the collected movement history information to the center communication unit 31, and transmits the same to the center server 1 through the center communication unit 31. Additionally, information about the date of first symptoms or the date of diagnosis of infection is also transmitted together with the infection report. Furthermore, in the case where the infection possibility notification system 100 handles a plurality of infectious diseases, the type of the infectious disease may also be transmitted to the center server 1, together with the infection report. Personal information that enables identification of the infected person is not transmitted together with the infection report.

Furthermore, the movement history collection unit 32 receives identification information on the infection report from the center server 1 through the center communication unit 31. The movement history collection unit 32 stores the identification information on the transmitted infection report in a predetermined storage area of the external storage device 303, for example.

The shop communication unit 33 communicates with the shop server 2. For example, the shop communication 33 receives the infection possibility notification from the shop server 2. The identification information on the infection report that cause the infection possibility notification is also received together with the infection possibility notification. The shop communication unit 33 compares the identification information on the infection report received together with the infection possibility notification with the identification information on the infection report recorded by the movement history collection unit 32, and in the case where the two match, the infection possibility notification that is received is discarded. The shop communication unit 33 compares the identification information on the infection report received together with the infection possibility notification with the identification information on the infection report recorded by the movement history collection unit 32, and in the case where the two do not match, the infection possibility notification that is received is output to the display control unit 34.

When input of the infection possibility notification is received from the shop communication unit 33, the display control unit 34 causes the infection possibility notification to be displayed on the display 305 with a touch panel.

The location information DB 35 is created in a predetermined storage area of the external storage device 303. The location information acquired by the location sensor 307 and the acquisition date/time of the location information are stored in the location information DB 35. The location sensor 307 may be set to valid or invalid based on user settings, for example. The location information is not acquired in the case where the location sensor 307 is invalid.

The center communication unit 31, the movement history collection unit 32, and the shop communication unit 33 are functional elements that are implemented by execution of a client application of the infection possibility notification system 100, for example. The display control unit 34 is a functional element of the OS, for example. The location information DB 35 is a functional element that is implemented by a control program of the location sensor 307, for example. However, the relationship between the functional elements and the programs is not limited to the above. The center communication unit 31, the movement history collection unit 32, and the shop communication unit 33 may be implemented by a web application that runs on a browser of the infection possibility notification system 100, without being limited to the client application, for example.

Next, the center server 1 includes, as functional elements, a shop identification unit 11, a server communication unit 12, a terminal communication unit 13, a map information DB 14, and a shop information DB 15. These functional elements are implemented by the CPU 101 of the center server 1 executing the control program of the infection possibility notification system 100, for example.

The terminal communication unit 13 communicates with the user terminal 3. In the first embodiment, the terminal communication unit 13 receives the infection report and the movement history information from the user terminal 3. The information pieces received from the user terminal 3 are output to the shop identification unit 11.

The server communication unit 12 communicates with the shop server 2. In the first embodiment, the server communication unit 12 transmits the infected-person visit notification to the shop server 2 specified by the shop identification unit 11.

The shop identification unit 11 receives input of the infection report and the movement history information received from the user terminal 3, and acquires, from the movement history information, information about the place visited by the infected person and information about the visit date/time, and the shop server 2 as the transmission destination of the infected-person visit notification. Furthermore, the shop identification unit 11 assigns identification information to the infection report that is received, and notifies the identification information to the user terminal 3 that is the transmission source of the infection report through the terminal communication unit 13.

For example, in the case where the movement history information is the history information on an acquisition of location information, the shop identification unit 11 refers to the map information DB 14, identifies a point of interest (POI) corresponding to the location information, and identifies the visited place of the infected person. Furthermore, the shop identification unit 11 identifies the acquisition date/time of the location information as the visit date/time by the infected person. In the case where there are a plurality of successive pieces of history information regarding an acquisition of location information indicating the same POI, a duration of a stay of the infected person is acquired as the visit date/time based on the acquisition dates/times of the plurality of pieces of location information. The duration of the stay is identified as a period from a start date/time of the stay to an end date/time of the stay. Furthermore, the shop identification unit 11 refers to the shop information DB 15, and identifies, as the transmission destination of the infected-person visit notification, the shop server 2 that is associated with the POI indicated by the location information.

For example, in the case where the movement history information is the shop-visit history information regarding a predetermined shop, the shop identification unit 11 identifies, as the visited place of the infected person, the shop that is indicated by the shop-visit history information regarding a predetermined shop. Furthermore, the shop identification unit 11 identifies, as the information about the visit date/time by the infected person, the date/time information that is included in the shop-visit history information regarding a predetermined shop. The date/time information that is included in the shop-visit history information regarding a predetermined shop is a recording date/time of check-in or a date/time of addition or use of points, for example. Furthermore, the shop identification unit 11 refers to the shop information DB 15, and identifies, as the transmission destination of the infected-person visit notification, the shop server 2 that is associated with the shop.

For example, in the case where the movement history information is the reservation history information regarding public transportation, the shop identification unit 11 acquires the transportation number of a bus or an airplane or the train name as the information about the visited place of the infected person. Furthermore, in the case where the reservation history information regarding the public transportation includes seat information, the seat information may be acquired as one piece of information about the visited place of the infected person. For example, the shop identification unit 11 identifies the boarding date/time as the visit date/time by the infected person. Moreover, the shop identification unit 11 identifies, as the transmission destination of the infected-person visit notification, a server of the corresponding public transportation. Information about the server of the public transportation is also stored in the shop information DB 15, for example.

For example, in the case where the movement history information is the payment history information regarding electronic money, the shop identification unit 11 identifies a shop receiving the payment as the visited place of the infected person. For example, the shop identification unit 11 identifies the payment date/time as the visit date/time by the infected person. Furthermore, the shop identification unit 11 refers to the shop information DB 15, and identifies the shop server 2 that is associated with the shop.

The shop identification unit 11 transmits, through the server communication unit 12, to the shop server 2 that is identified as the transmission destination of the infected-person visit notification, the infected-person visit notification, the identification information on the infection report, the information about the visited place of the infected person, and the information about the visit date/time by the infected person. Additionally, there may be one or more transmission destinations for the infected-person visit notification.

The map information DB 14 and the shop information DB 15 are created in a predetermined storage area of the external storage device 103. The map information DB 14 holds map information. The shop information DB 15 holds information about the shop server 2. Information about the shop server 2 includes information about an associated shop, contact information on the shop server 2, and the like, for example. Information about an associated shop is location information, name or identification information on the shop, for example.

Next, as functional elements, the shop server 2 includes a customer identification unit 21, a server communication unit 22, a customer notification unit 23, a customer information DB 24, and a shop-visit history information DB 25. For example, the customer identification unit 21, the server communication unit 22, and the customer notification unit 23 are implemented by the CPU 201 of the shop server 2 executing a program for coordinating with the center server 1 of the infection possibility notification system 100. The customer information DB 24 and the shop-visit history information DB 25 are implemented by executing a customer information management program of the shop server 2, for example.

The server communication unit 22 communicates with the center server 1. In the first embodiment, the server communication unit 22 receives the infected-person visit notification from the center server 1. The identification information on the infection report, information about the visited place of the infected person, and information about the visit date/time are also received together with the infected-person visit notification. Information pieces received from the center server 1 are output to the customer identification unit 21.

The customer notification unit 23 communicates with the user terminal 3 of a customer. In the first embodiment, the customer notification unit 23 transmits the infection possibility notification to the user terminal 3. The infection possibility notification is input from the customer identification unit 21.

The customer identification unit 21 identifies the customer who was at the visited place of the infected person at the time of visit by the infected person. For example, the customer identification unit 21 refers to the shop-visit history information DB 25, and identifies the customer for whom there is the shop-visit history information regarding the visited place notified by the center server 1, in a period that is obtained by adding a predetermined length of time to before and after the visit date/time notified by the center server 1. The time length that is added to the visit date/time is set according to the characteristics of each shop in units of 10 minutes, 15 minutes, 30 minutes or 1 hour, for example.

The customer identification unit 21 transmits the infection possibility notification to the user terminal 3 of the customer who is identified. The identification information on the infection report, the type of the infectious disease, the visited place of the infected person, and the date of visit by the infected person are also transmitted together with the infection possibility notification, for example. Furthermore, the infection possibility notification is transmitted by push notification, email or short messaging, for example. Alternatively, in the case where the client application of the infection possibility notification system 100 is a web application, the infection possibility notification is transmitted to the user terminal 3 in a session of a browser.

The customer information DB 24 and the shop-visit history information DB 25 are created in a predetermined storage area of the external storage device 203. The customer information DB 24 holds information about customers. Information about a customer includes identification information, name, address, date of birth, telephone number as contact information, email address, and the like of the customer, for example. Identification information on a customer is identification information that is assigned to the customer in the shop server 2 for identification of the customer.

FIG. 4 is a diagram illustrating an example of information that is held in the shop-visit history information DB 25. The shop-visit history information DB 25 holds the shop-visit history information regarding the shop that is managed by the shop server 2. The shop-visit history information that is stored in the shop-visit history information DB 25 includes the following fields: a timestamp, a shop ID, a customer ID, and a type of event. Information that is held in the shop-visit history information DB 25 is an example of "visit history information".

The date/time of an acquisition of the shop-visit history information is stored in the field "timestamp". The identification information on the shop is stored in the field "shop ID". The identification information on the customer is stored in the field "customer ID". Information indicating the type of event that triggered generation of the shop-visit history information is stored in the field "type of event". The type of event may be check-in, use or addition of points, or the like, for example. Check-in is a record of a visit to the shop that is recorded through an application for the user terminal 3 in relation to the shop that is managed by the shop server 2, or that is recorded in an apparatus that is installed at the shop with the user terminal 3, a rewards card or the like, for example. Use or addition of points is recorded by a cash register when a rewards card is presented at the time of purchase of a product, for example. Additionally, the type of event is not limited to those mentioned above.

The customer identification unit 21 refers to the shop-visit history information DB 25 and identifies the identification information on a customer who visited the shop corresponding to the visited place of an infected person in a period that includes the visit date/time by the infected person and a predetermined length of time before and after the visit date/time, and acquires, from the customer information DB 24, contact information corresponding to the identification information on the customer who is identified. Additionally, information pieces that are stored in the shop-visit history information DB 25 are not limited to those illustrated in FIG. 4. For example, in the case where the shop server 2 is a server of public transportation, a database holding boarding reservation information for the public transportation is used instead of the shop-visit history information DB 25. For example, in the case where the shop server 2 is a server that manages electronic money payment, a database holding information on a payment with electronic money is used instead of the shop-visit history information DB 25.

Figure 5:
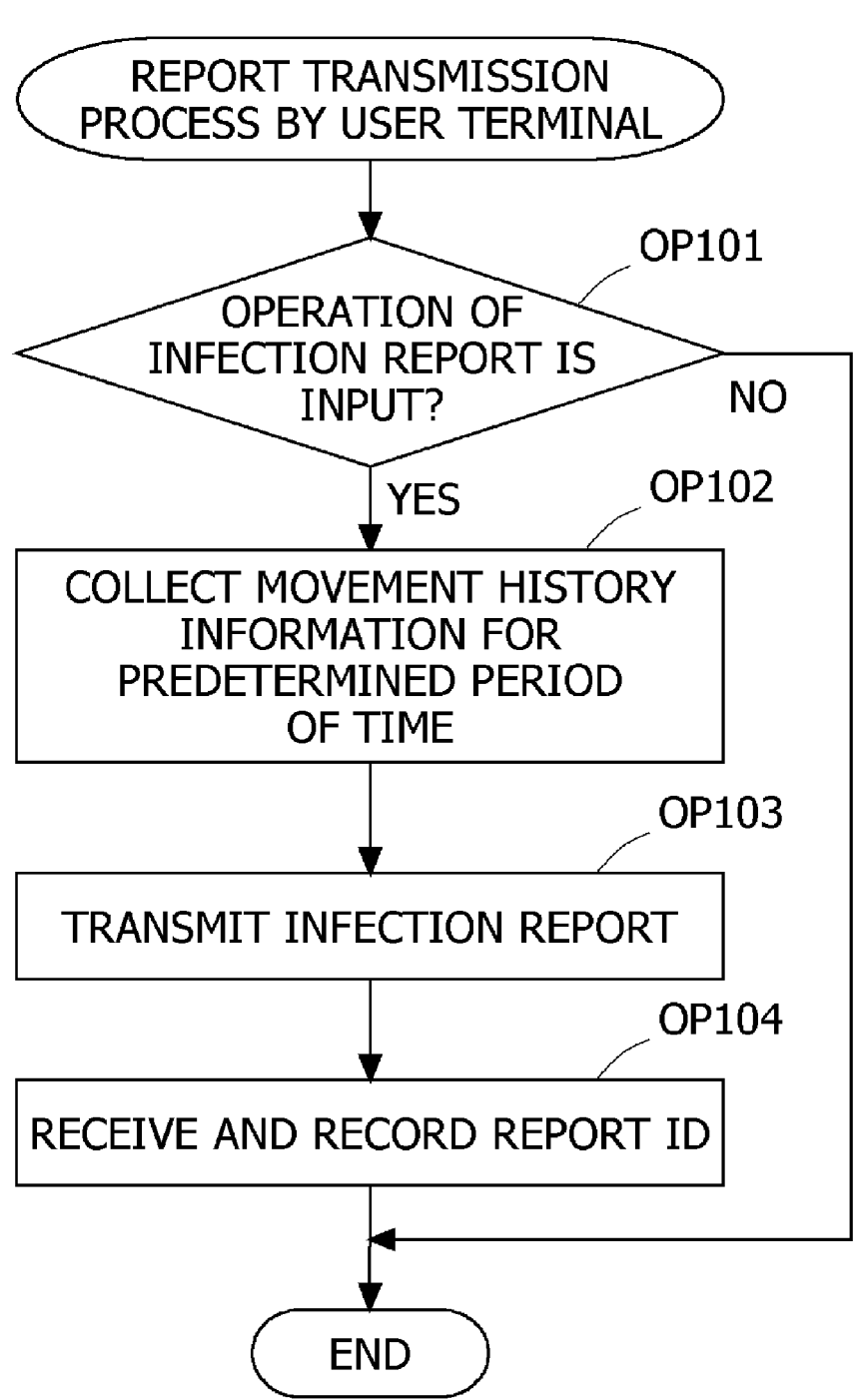
FIG. 5 is an example of a flowchart of a report transmission process by the user terminal.

FIG. 5 is an example of a flowchart of a report transmission process by the user terminal 3. The report transmission process is a process of transmitting the infection report to the center server 1. The process illustrated in FIG. 5 is a process that is performed by the user terminal 3A in FIG. 1, for example. The process illustrated in FIG. 5 is repeated every predetermined period of time, for example. The performer of the process illustrated in FIG. 5 is the CPU 301 of the user terminal 3, but a functional element will be described to be the performer for the sake of convenience. A description will be given for subsequent flowcharts by also taking a functional element as the performer.

In OP101, the movement history collection unit 32 determines whether a user operation of an infection report is input to the user terminal 3. In the case where a user operation of an infection report is input to the user terminal 3 (OP101: YES), the process proceeds to OP102. In the case where a user operation of an infection report is not input to the user terminal 3 (OP101: NO), the process illustrated in FIG. 5 is ended.

In OP102, the movement history collection unit 32 collects the movement history information for a predetermined period of time. Details of collection of the movement history information are as described above. In OP103, the movement history collection unit 32 transmits the infection report and the movement history information to the center server 1 through the center communication unit 31. In OP104, the movement history collection unit 32 receives the identification information on the infection report transmitted in OP103, from the center server 1 and through the center communication unit 31, and records the identification information. The process illustrated in FIG. 5 is then ended.

Figure 6:
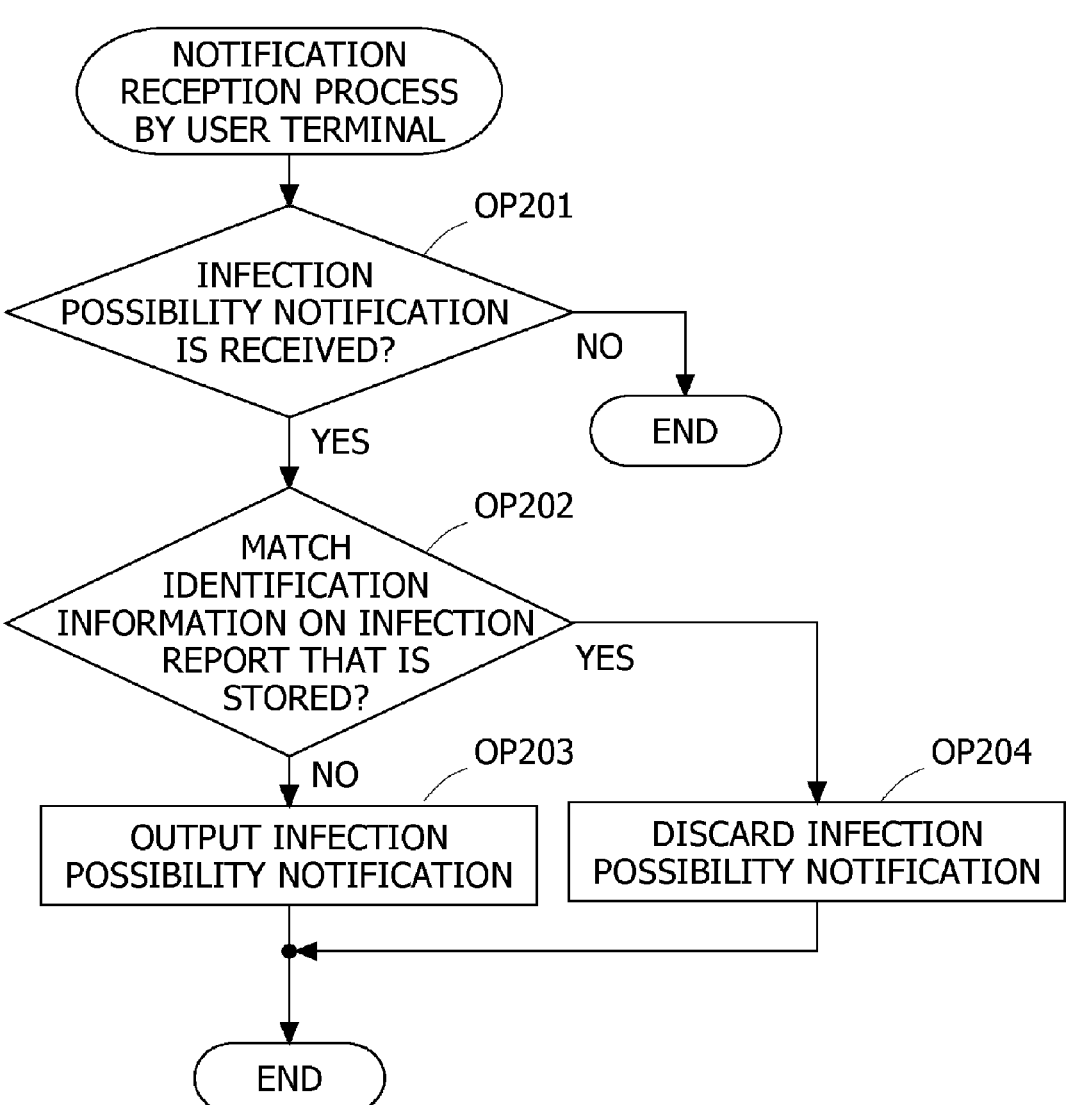
FIG. 6 is an example of a flowchart of a notification reception process by the user terminal.

FIG. 6 is an example of a flowchart of a notification reception process by the user terminal 3. The notification reception process is a process that is performed in a case where the infection possibility notification is received from the shop server 2. The process illustrated in FIG. 6 is a process that is performed by the user terminal 3B in FIG. 1, for example. The process illustrated in FIG. 6 is repeated every predetermined period of time, for example.

In OP201, the shop communication unit 33 determines whether an infection possibility notification is received from the shop server 2. In the case where an infection possibility notification is received from the shop server 2 (OP201: YES), the process proceeds to OP202. In the case where an infection possibility notification is not received from the shop server 2 (OP201: NO), the process illustrated in FIG. 6 is ended.

In OP202, the shop communication unit 33 determines whether the identification information on the infection report that is received together with the infection possibility notification matches the identification information on the infection report that is stored in a predetermined storage area of the external storage device 303. In the case where the two match (OP202: YES), the process proceeds to OP204. In the case where the two are different (OP202: NO), the process proceeds to OP203.

In OP203, the shop communication unit 33 outputs the infection possibility notification to the display control unit 34, and notifies the user of possible infection. The process illustrated in FIG. 6 is then ended.

In OP204, the shop communication unit 33 discards the infection possibility notification that is received. In this case, the user is not notified of possible infection. The process illustrated in FIG. 6 is then ended.

Figure 7:
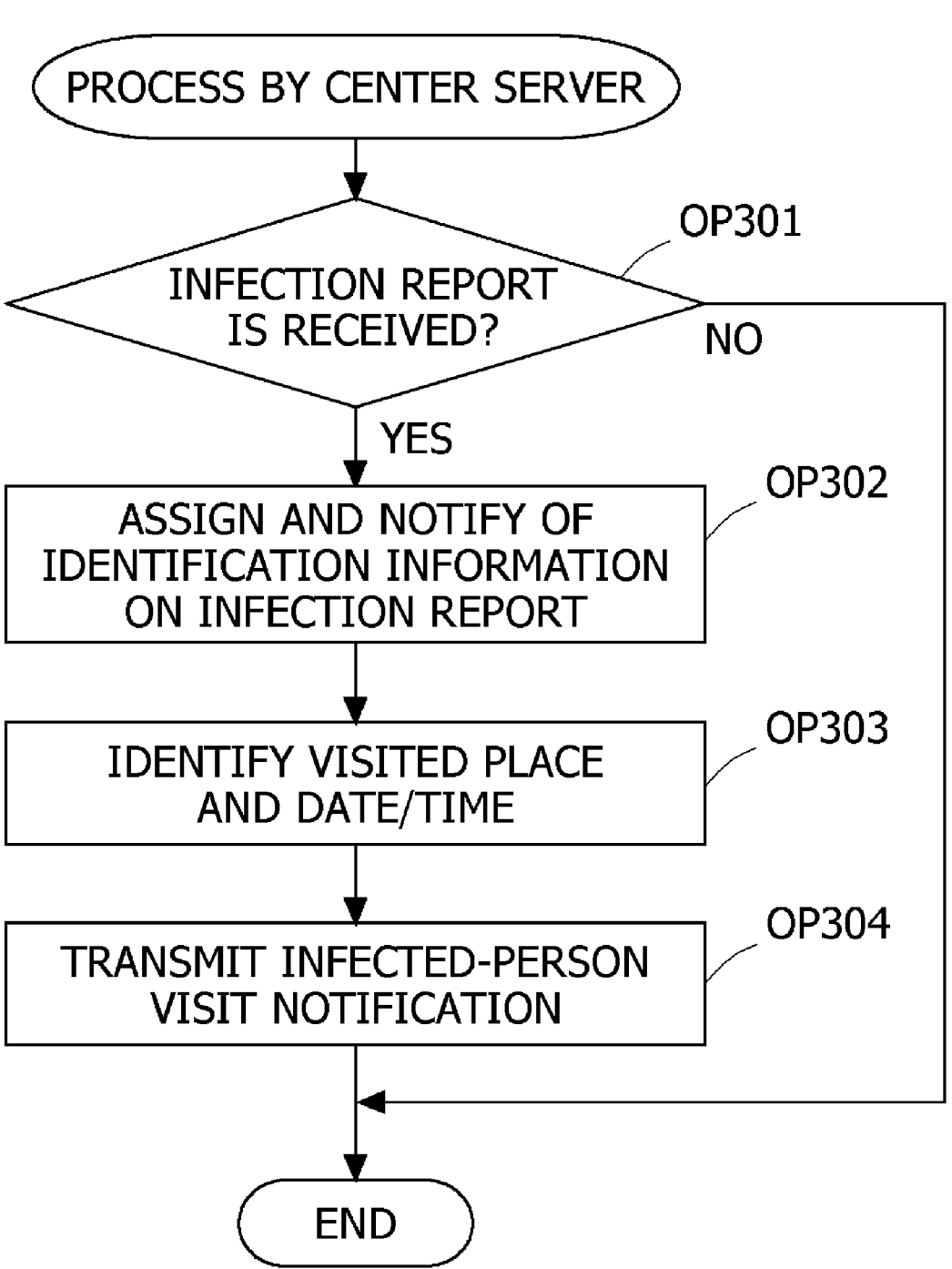
FIG. 7 is an example of a flowchart of a process by the center server.

FIG. 7 is an example of a flowchart of a process by the center server 1. The process illustrated in FIG. 7 is repeated every predetermined period of time, for example.

In OP301, the shop identification unit 11 determines whether an infection report is received from the user terminal 3 through the terminal communication unit 13. In the case where an infection report is received from the user terminal 3 (OP301: YES), the process proceeds to OP302. In the case where an infection report is not received from the user terminal 3 (OP301: NO), the process illustrated in FIG. 7 is ended.

In OP302, the shop identification unit 11 assigns identification information to the infection report that is received, and notifies the user terminal that is the transmission source of the infection report of the identification information.

In OP303, the shop identification unit 11 identifies, from the movement history information on the infected person that is received, the visited place of the infected person and the visit date/time, and the transmission destination of the infected-person visit notification. In OP304, the shop identification unit 11 transmits, to the transmission destination that is identified, through the server communication unit 12, the infected-person visit notification, information about the visited place of the infected person and information about the visit date/time. The process illustrated in FIG. 7 is then ended.

Figure 8:
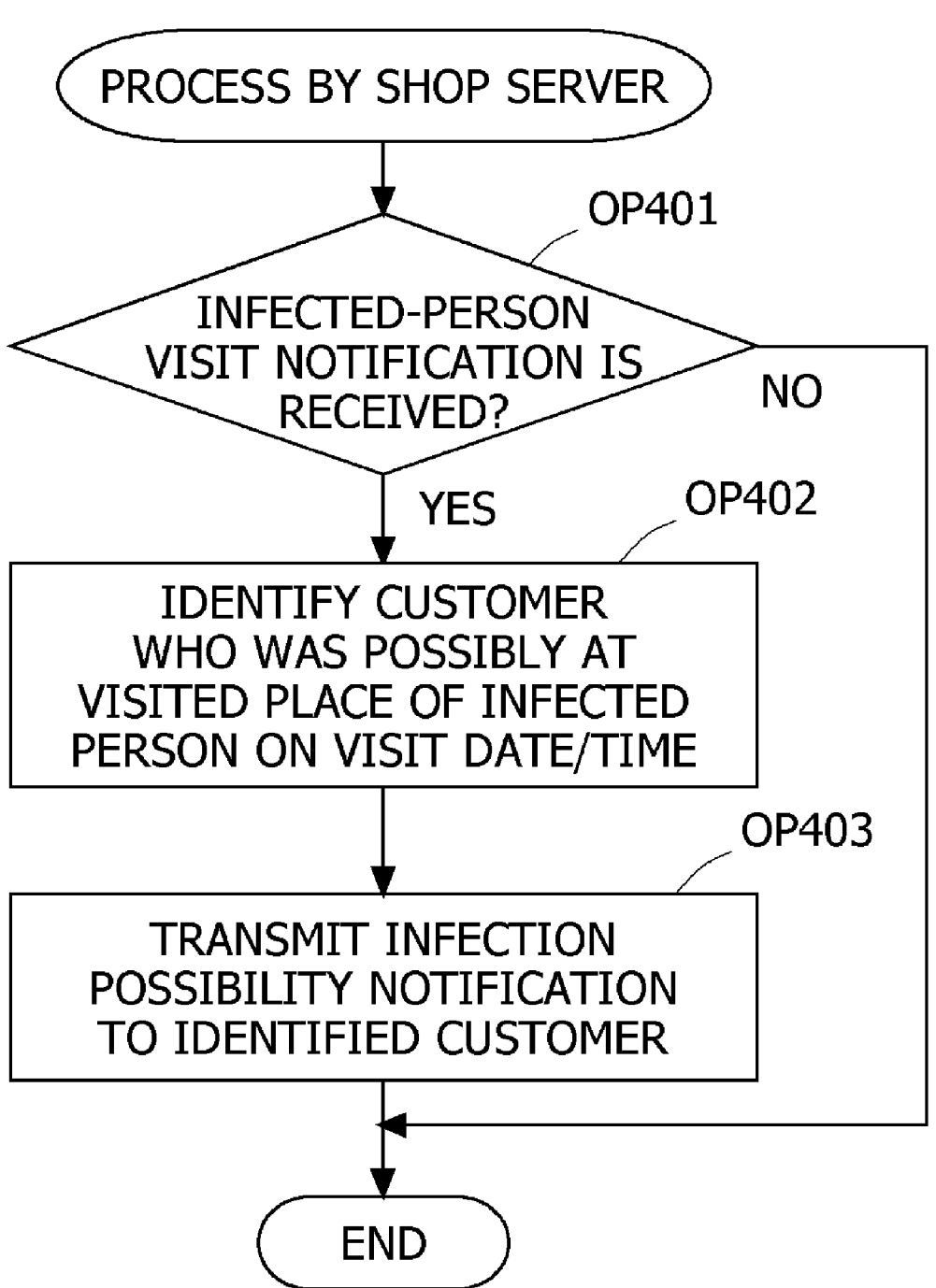
FIG. 8 is an example of a flowchart of a process by the shop server.

FIG. 8 is an example of a flowchart of a process by the shop server 2. The process illustrated in FIG. 8 is repeated every predetermined period of time, for example.

In OP401, the customer identification unit 21 determines whether an infected-person visit notification is received from the center server 1 through the server communication unit 22. In the case where an infected-person visit notification is received from the center server 1 (OP401: YES), the process proceeds to OP402. In the case where an infected-person visit notification is not received from the center server 1 (OP401: NO), the process illustrated in FIG. 8 is ended.

In OP402, the customer identification unit 21 refers to the shop-visit history information DB 25, and identifies one or more customers who visited the visited place of the infected person that is received together with the infected-person visit notification, in a period that is obtained by adding a predetermined length of time to before and after the visit date/time by the infected person. In OP403, the customer identification unit 21 transmits the infection possibility notification to one or more terminals 3 of the one or more customers who are identified, through the customer notification unit 23. The process illustrated in FIG. 8 is then ended.

Additionally, the processes by the center server 1, the shop server 2, and the user terminal 3 that are illustrated in FIGS. 5 to 8 are merely examples, and are not limited to the processes illustrated in FIGS. 5 to 8.

Operations and Effects of First Embodiment

In the first embodiment, a user who was possibly at the same place and at the same time as an infected person with a predetermined infectious disease may be notified of the possibility of being infected. Furthermore, the customer is identified based on the movement history information from the infected person, and personal information on the infected person is not used, and thus, the infected person may be prevented from being identified. Moreover, the customer information that is registered in advance with the shop server 2 with the consent of the user is not transmitted anywhere from the shop server 2, and thus, a user who was possibly at the same place and at the same time as the infected person, or in other words, a user who is possibly infected, may be prevented from being identified.

Furthermore, an infected person who reported infection is possibly identified by the shop server 2 as a user who was possibly at the same place and at the same time as the infected person. In this case, the user terminal 3 of the infected person who performed the infection report receives the infection possibility notification from a plurality of shop servers 2, and the user who is the infected person may feel annoyed. When the user terminal 3 that is the transmission source of an infection report is notified of the identification information on the infection report together with the infection possibility notification, the user terminal 3 receiving the infection possibility notification may perform filtering using the identification information on the infection report, and the infected person may be prevented from being notified of the infection possibility notification.

Other Embodiments

The embodiment described above is an example, and the present disclosure may be changed and carried out as appropriate without departing from the gist of the present disclosure.

The method used by the shop server 2 to identify the customer who was at the visited place of an infected person on the visit date/time by the infected person is not limited to the method described above, and any method may be used. For example, in the case where a photograph of the face of a customer is registered as the customer information, a customer who was at the visited place of an infected person on the visit date/time by the infected person may be identified from an image of a camera installed at the shop using a facial recognition process that uses the face image.

The processes and means described in the present disclosure may be freely combined to the extent that no technical conflict exists.

A process which is described to be performed by one device may be performed divided among a plurality of devices. Processes described to be performed by different devices may be performed by one device. Each function is to be implemented by which hardware component (server component) in a computer system may be flexibly changed.

The present disclosure may also be implemented by supplying a computer program for implementing a function described in the embodiment above to a computer, and by reading and executing the program by at least one processor of the computer. Such a computer program may be provided to a computer by a non-transitory computer-readable storage medium which is connectable to a system bus of a computer, or may be provided to a computer through a network. The non-transitory computer-readable storage medium may be any type of disk such as a magnetic disk (floppy (registered trademark) disk, a hard disk drive (HDD), etc.), an optical disk (CD-ROM, DVD disk, Blu-ray disk, etc.), a read only memory (ROM), a random access memory (RAM), an EPROM, an EEPROM, a magnetic card, a flash memory, an optical card, and any type of medium which is suitable for storing electronic instructions.

What is claimed is:

1. An information processing system comprising:
a first server;
a plurality of second servers that are associated with respective predetermined places; and
a user terminal including a third processor, wherein:
the first server includes a first processor configured to:
acquire movement history information on an infected person who is proven to be infected with a predetermined infectious disease;
identify, based on the movement history information, a first place that the infected person visited and a first visit date and time by the infected person; and
notify a second server associated with the first place of information about the first place and information about the first visit date and time; and
the plurality of second servers each include a second processor configured to:

based on visit history information including a visit date and time of the predetermined place by a user who is associated with the predetermined place, identify a first user who visited the predetermined place, as the first place, on the first visit date and time of the infected person notified from the first server; and notify the first user of possibility of being infected with the predetermined infectious disease;

the first processor is further configured to:

receive an infection report from a user terminal of the infected person, together with the movement history information;

assign identification information to the infection report;

notify the user terminal of the infected person of the identification information; and notify the second server associated with the first place of the identification information, together with the information about the first place and the information about the first visit date and time;

the second processor is further configured to:

transmit, to a user terminal of the first user, the identification information together with a notification about the possibility of being infected with the predetermined infectious disease; and the third processor is further configured to:

transmit the infection report to the first server;

receive, from the first server, first identification information assigned to the infection report;

receive, from one of the plurality of second servers, the identification information together with the notification about the possibility of being infected with the predetermined infectious disease;

compare the identification information received from the one of the plurality of second servers with the first identification information received from the first server;

discard the notification received from the one of the plurality of second servers in a case where the identification information received from the one of the plurality of second servers is identical to the first identification information received from the first server; and output the notification in a case where the identification information received from the one of the plurality of second servers is not identical to the first identification information received from the first server.

2. The information processing system according to claim 1, wherein the movement history information is anonymous information.

3. The information processing system according to claim 1, wherein:

the movement history information includes location information and an acquisition date and time of the location information; and the first processor is configured to identify the first place and the first visit date and time based on the movement history information and map information.

4. The information processing system according to claim 1, wherein at least one of the movement history information and the visit history information is information about a payment history.

5. The information processing system according to claim 1, wherein at least one of the movement history information and the visit history information is history information on a visit to the predetermined place recorded by a user terminal through an application related to the predetermined place.

6. The information processing system according to claim 1, wherein:

at least one of the movement history information and the visit history information is boarding reservation information including at least a transportation number or a train name of public transportation and a boarding date;

the information about the first place is information indicating the transportation number or the train name; and the information about the first visit date/time is the information indicated by the transportation number or the train name and the boarding date.

7. The information processing system according to claim 1, wherein the second processor identifies, as the first user, a user corresponding to the visit history information that includes a visit date/time of the predetermined place that is included in a predetermined period of time including the first visit date/time.

8. An information processing method that is performed by a first server, a plurality of second servers that are associated with respective predetermined places and a user terminal, wherein:

the first server is configured to:

acquire movement history information on an infected person who is proven to be infected with a predetermined infectious disease;

identify, based on the movement history information, a first place that the infected person visited and a first visit date and time; and notify a second server associated with the first place of information about the first place and information about the first visit date and time; and the plurality of second servers are each configured to:

based on visit history information including a visit date and time of the predetermined place by a user who is associated with the predetermined place, identify a first user who visited the predetermined place, as the first place, on the first visit date/time of the infected person notified from the first server; and notify the first user of possibility of being infected with the predetermined infectious disease;

the first server is further configured to:

receive an infection report from a user terminal of the infected person, together with the movement history information;

assign identification information to the infection report;

notify the user terminal of the infected person of the identification information; and notify the second server associated with the first place of the identification information, together with the information about the first place and the information about the first visit date and time;

the second server is further configured to:

transmit, to a user terminal of the first user, the identification information together with a notification about the possibility of being infected with the predetermined infectious disease; and the user terminal of the first user and the user terminal of the infected person are each further configured to:

transmit the infection report to the first server;

receive, from the first server, first identification information assigned to the infection report;

receive, from one of the plurality of second servers, the identification information together with the notification about the possibility of being infected with the predetermined infectious disease;

compare the identification information received from the one of the plurality of second servers with the first identification information received from the first server;

discard the notification received from the one of the plurality of second servers in a case where the identification information received from the one of the plurality of second servers is identical to the first identification information received from the first server; and output the notification in a case where the identification information received from the one of the plurality of second servers is not identical to the first identification information received from the first server.

9. The information processing method according to claim 8, wherein the movement history information is anonymous information.

10. The information processing method according to claim 8, wherein:

the movement history information includes location information and an acquisition date and time of the location information; and the first server identifies the first place and the first visit date and time based on the movement history information and map information.

11. The information processing method according to claim 8, wherein at least one of the movement history information and the visit history information is information including a record of a visit to the predetermined place made by a user terminal through an application related to the predetermined place.

12. The information processing method according to claim 8, wherein:

at least one of the movement history information and the visit history information is boarding reservation information including at least a transportation number or a train name of public transportation and a boarding date;

the information about the first place is information indicating the transportation number or the train name; and the information about the first visit date/time is the information indicated by the transportation number or the train name and the boarding date.

13. One or more non-transitory computer-readable recording media stored with one or more programs which, when executed by a first server, a plurality of second servers that are associated with respective predetermined places and a user terminal:

cause the first server to:

acquire movement history information on an infected person who is proven to be infected with a predetermined infectious disease;

identify, based on the movement history information, a first place that the infected person visited and a first visit date and time; and notify a second server associated with the first place of information about the first place and information about the first visit date and time;

cause each of the plurality of the second servers to:

based on visit history information including a visit date and time of the predetermined place by a user who is associated with the predetermined place, identify a first user who visited the predetermined place, as the first place, on the first visit date and time of the infected person notified from the first server; and notify the first user of possibility of being infected with the predetermined infectious disease;

further cause the first server to:

receive an infection report from a user terminal of the infected person, together with the movement history information;

assign identification information to the infection report;

notify the user terminal of the infected person of the identification information; and notify the second server associated with the first place of the identification information, together with the information about the first place and the information about the first visit date and time;

further cause the second server to:

transmit, to a user terminal of the first user, the identification information together with a notification about the possibility of being infected with the predetermined infectious disease; and cause the user terminal of the first user and the user terminal of the infected person to:

transmit the infection report to the first server;

receive, from the first server, first identification information assigned to the infection report;

receive, from one of the plurality of second servers, the identification information together with the notification about the possibility of being infected with the predetermined infectious disease;

compare the identification information received from the one of the plurality of second servers with the first identification information received from the first server;

discard the notification received from the one of the plurality of second servers in a case where the identification information received from the one of the plurality of second servers is identical to the first identification information received from the first server; and output the notification in a case where the identification information received from the one of the plurality of second servers is not identical to the first identification information received from the first server.

* * * * *